United States Patent
Larsen et al.

(10) Patent No.: US 8,227,250 B2
(45) Date of Patent: Jul. 24, 2012

(54) LYSING REAGENT, CARTRIDGE AND AUTOMATIC ELECTRONIC CELL COUNTER FOR SIMULTANEOUS ENUMERATION OF DIFFERENT TYPES OF WHITE BLOOD CELLS

(75) Inventors: Ulrik Darling Larsen, Holte (DK); Stine Hallberg Hansen, Farum (DK); Björn Ekberg, Malmö (SE)

(73) Assignee: Koninklijke Philips Electronics N.V., Eindhoven (NL)

( * ) Notice: Subject to any disclaimer, the term of this patent is extended or adjusted under 35 U.S.C. 154(b) by 826 days.

(21) Appl. No.: 10/517,383

(22) PCT Filed: Jun. 11, 2003

(86) PCT No.: PCT/DK03/00383
§ 371 (c)(1), (2), (4) Date: Jun. 27, 2005

(87) PCT Pub. No.: WO03/104771
PCT Pub. Date: Dec. 18, 2003

(65) Prior Publication Data
US 2006/0177347 A1    Aug. 10, 2006

Related U.S. Application Data

(60) Provisional application No. 60/387,407, filed on Jun. 11, 2002.

(30) Foreign Application Priority Data

Feb. 5, 2003  (DK) .................................. 2003 00159

(51) Int. Cl.
*G01N 33/50* (2006.01)
*G01N 33/00* (2006.01)

(52) U.S. Cl. ..................... 436/63; 436/17; 42/73; 42/81; 42/549

(58) Field of Classification Search .................... 422/73, 422/81, 549; 436/17, 63
See application file for complete search history.

(56) References Cited

U.S. PATENT DOCUMENTS 2,656,508 A    10/1953    Coulter
3,122,431 A    2/1964    Coulter et al.
(Continued)

FOREIGN PATENT DOCUMENTS

EP    0193394 B1    7/1991
(Continued)

OTHER PUBLICATIONS

Volker Kachel, "Electrical Resistance Pulse Sizing: Coulter-Sizing", Flow Cytometry and Sorting, pp. 45-80, 2nd ed., 1990 Wiley-Liss Inc.

(Continued)

*Primary Examiner* — Krishnan S Menon
*Assistant Examiner* — Rebecca M Fritchman

(57) ABSTRACT

The present invention relates to a lysing reagent for use in the simultaneous automatic electronic enumeration and volumetric discrimination of different types of blood cells, such as leukocytes, thrombocytes, etc, in blood. Further, the present invention relates to a Coulter (impedance) counting apparatus containing the lysing reagent, for example a Coulter counting apparatus with a disposable cartridge for characterizing cells suspended in a liquid, especially a self-contained disposable cartridge for single-use analysis, such as for single-use analysis of a small quantity of whole blood.

25 Claims, 9 Drawing Sheets

U.S. PATENT DOCUMENTS

Figure 1:
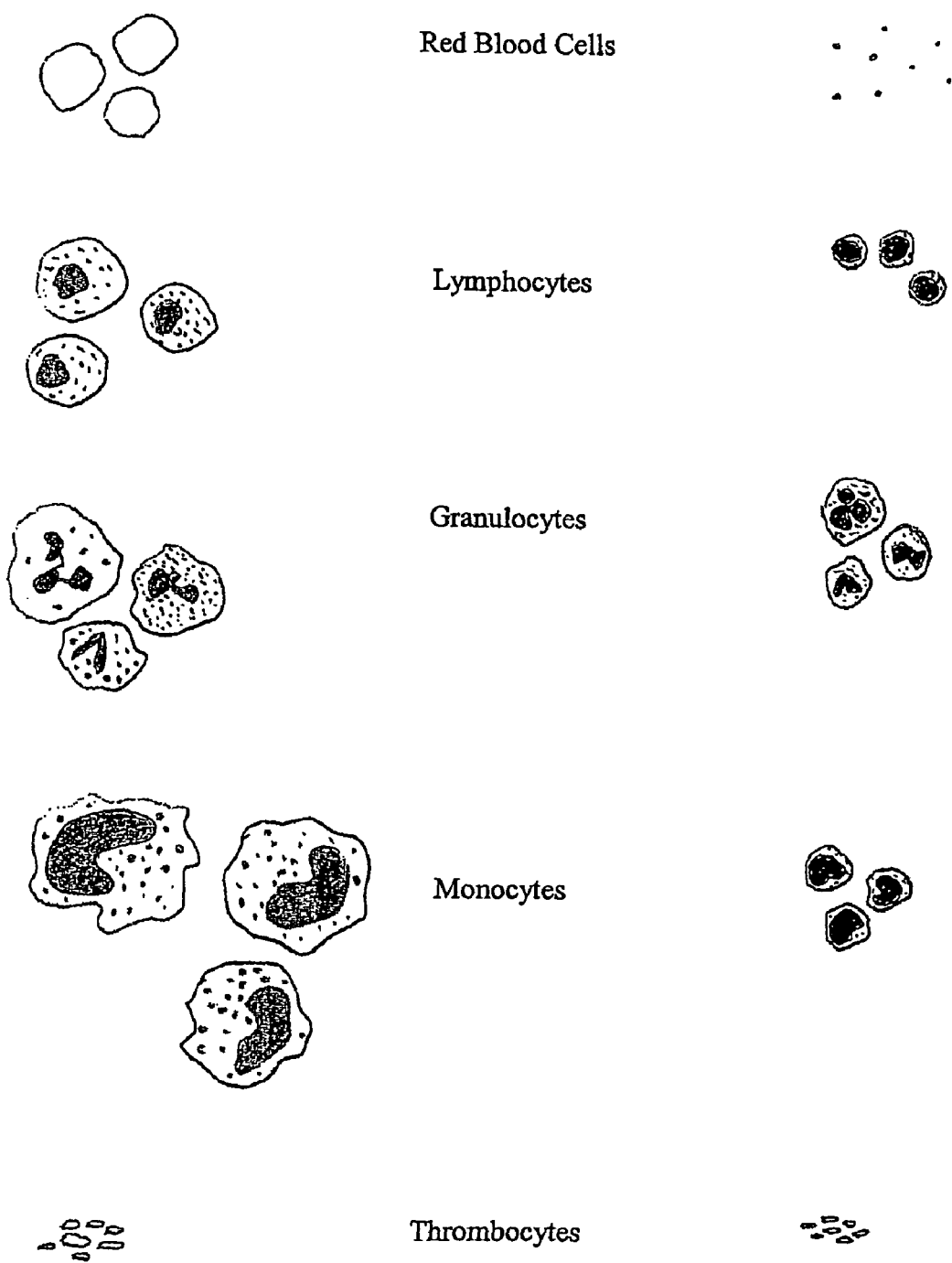

| | | | |
|---|---|---|---|
| 3,395,343 A | | 7/1968 | Morgan et al. |
| 3,549,994 A | | 12/1970 | Rothermel et al. |
| 3,902,115 A | | 8/1975 | Hogg et al. |
| 3,958,177 A | | 5/1976 | Reeves et al. |
| 4,014,611 A | | 3/1977 | Simpson et al. |
| 4,346,018 A | | 8/1982 | Carter et al. |
| 4,485,175 A | | 11/1984 | Ledis et al. |
| 4,521,518 A | * | 6/1985 | Carter et al. ............... 436/10 |
| 4,521,729 A | | 6/1985 | Kiesewetter et al. |
| 4,528,274 A | | 7/1985 | Carter et al. |
| 4,600,880 A | | 7/1986 | Doutre et al. |
| 4,607,526 A | | 8/1986 | Bachenheimer et al. |
| 4,706,207 A | | 11/1987 | Hennessy et al. |
| 4,738,827 A | | 4/1988 | Pierotti |
| 4,745,071 A | | 5/1988 | Lapicola et al. |
| 4,751,179 A | | 6/1988 | Ledis et al. |
| 4,760,328 A | | 7/1988 | Groves |
| 4,835,457 A | | 5/1989 | Hanss et al. |
| 4,926,114 A | | 5/1990 | Doutre |
| 4,962,038 A | | 10/1990 | Carter et al. |
| 5,045,474 A | * | 9/1991 | Becker et al. ............... 436/63 |
| 5,077,017 A | | 12/1991 | Gorin et al. |
| 5,104,813 A | | 4/1992 | Besemer et al. |
| 5,198,749 A | | 3/1993 | Guthrie et al. |
| 5,230,866 A | | 7/1993 | Shartle et al. |
| 5,231,005 A | | 7/1993 | Russell et al. |
| 5,241,262 A | | 8/1993 | Guthrie et al. |
| 5,257,984 A | | 11/1993 | Kelley |
| 5,316,951 A | | 5/1994 | Carver, Jr. et al. |
| 5,334,502 A | * | 8/1994 | Sangha ............... 435/7.21 |
| 5,348,859 A | | 9/1994 | Brunhouse et al. |
| 5,393,496 A | * | 2/1995 | Seymour ............... 422/101 |
| 5,500,992 A | | 3/1996 | Barnes et al. |
| 5,501,982 A | * | 3/1996 | Saldivar et al. ............... 436/150 |
| 5,623,200 A | | 4/1997 | Ogino |
| 5,716,852 A | | 2/1998 | Yager et al. |
| 5,731,206 A | * | 3/1998 | Ledis et al. ............... 436/17 |
| 5,763,280 A | | 6/1998 | Li et al. |
| 5,804,022 A | | 9/1998 | Kaltenbach et al. |
| 5,834,315 A | | 11/1998 | Riesgo et al. |
| 5,840,515 A | | 11/1998 | Provost |
| 5,882,934 A | * | 3/1999 | Li et al. ............... 436/66 |
| 5,911,871 A | | 6/1999 | Preiss et al. |
| 5,979,251 A | | 11/1999 | James et al. |
| 6,111,398 A | | 8/2000 | Graham |
| 6,159,740 A | | 12/2000 | Hudson et al. |
| 6,230,896 B1 | | 5/2001 | Lambert |
| 6,251,615 B1 | * | 6/2001 | Oberhardt ............... 435/7.21 |
| 6,319,209 B1 | | 11/2001 | Kriz |
| 6,387,328 B1 | * | 5/2002 | Berndtsson ............... 422/73 |
| 6,663,833 B1 | * | 12/2003 | Stave et al. ............... 422/81 |
| 6,852,284 B1 | | 2/2005 | Holl et al. |

FOREIGN PATENT DOCUMENTS

| | | |
|---|---|---|
| EP | 0 549 414 A1 | 12/1992 |
| EP | 0 844 475 A2 | 11/1997 |
| EP | 1 182 457 A1 | 8/2000 |
| EP | 1 182 457 A | 2/2002 |
| GB | 2 232 769 A | 12/1990 |
| GR | 1 002 424 | 8/1996 |
| JP | 5915849 A | 1/1984 |
| JP | 61205844 | 9/1986 |
| JP | 7301595 | 11/1995 |
| JP | 8015125 | 1/1996 |
| JP | 9304265 | 11/1997 |
| JP | 2002515601 | 5/2002 |
| WO | 9960379 | 11/1999 |
| WO | WO 00/07254 | 2/2000 |
| WO | WO 01 11338 A | 2/2001 |
| WO | WO 01/11338 A1 | 2/2001 |
| WO | WO 01/69292 A2 | 9/2001 |
| WO | WO 02 089670 A | 11/2002 |
| WO | WO 02/089670 A1 | 11/2002 |
| WO | 03044488 A1 | 5/2003 |
| WO | 03104772 A1 | 12/2003 |
| WO | 2004061411 A2 | 7/2004 |

OTHER PUBLICATIONS

Ed. M.M. Wintrobe et al., "Clinical Hematology", pp. 3-9, 1981, 8th ed., Lea & Febiger, Philadelphia, USA.

M. Madou, "Fundamenetals of Microfabrication", pp. 29-32, 66-70, 145, and 163-164, CRC Press LLC, 1997, ISBN 0-8493-9451-1.

Stevens, "Fundamentals of Clinical Hematology", pp. 6-7, and 301-304, W.B. Saunders Company, ISBN 0-7216-4177-6, Philadelphia, USA.

A.Y. Fu et al., "A Microfabricated fluorescene-activated cell sorter", Nature Biotechnology, vol. 17, Nov. 1999, pp. 1109-1111.

B.K. Gale et al., Micromachined Electrical Field-Flow Fractionation (u-EFFF) System:, Proceedings of the IEEE Annual International Workshop; pp. 119-124; Jan. 1997.

* cited by examiner

WBC = Leukocytes

LYM = Lymphocytes

GRN = Granulocytes

MON = Monocytes

PLT = Thrombocytes

LYSING REAGENT, CARTRIDGE AND AUTOMATIC ELECTRONIC CELL COUNTER FOR SIMULTANEOUS ENUMERATION OF DIFFERENT TYPES OF WHITE BLOOD CELLS

CROSS REFERENCE TO RELATED APPLICATIONS

This application claims priority under 35 U.S.C. 119 to Danish application PA 2003 00159 filed on Feb. 5, 2003, and under 35 U.S.C. 119(e)(1) to U.S. Provisional application Ser. No. 60/387,407 filed on Jun. 11, 2002, which are hereby incorporated by reference.

A lysing reagent for the simultaneous enumeration of different types of white blood cells.

The present invention relates to a lysing reagent for use in the simultaneous automatic electronic enumeration and volumetric discrimination of different types of blood cells, such as leukocytes, thrombocytes, etc, in blood. Further, the present invention relates to a Coulter (impedance) counting apparatus containing the lysing reagent, for example a Coulter counting apparatus with a disposable cartridge for characterizing cells suspended in a liquid, especially a self-contained disposable cartridge for single-use analysis, such as for single-use analysis of a small quantity of whole blood.

The three types of blood cells erythrocytes, leukocytes and thrombocytes differ in a) size, b) occurrence and c) structure.

a) Their size, expressed as diameter, ranges from 2 μm for the smallest thrombocytes to 20 μm for the largest leukocytes.

b) Their occurrence normally ranges from typically 4.109/L blood for leukocytes to typically 4.1012/L blood for erythrocytes.

c 1) The thrombocytes contain organelles such as microfilaments, granules (including so called dense-bodies) and mitochondria, surrounded by a cell membrane. This membrane is in its turn surrounded by an so-called surface coat.

c 2) The most distinct leukocyte organelle is the microscopically visible granule, which has different structure in the different leukocyte sub-populations.

c 3) The erythrocytes cell membrane does, however, not surround any organelles as mentioned above. Finally, the three types of blood cells have different shape. (Clinical Haematology, Ed. M. M. Wintrobe, 1981, 8th Ed, Lia & Febiger, Philadelphia, USA)

Information on the content of leukocytes, their subpopulations and thrombocytes is an important tool for the physician in order to diagnose different diseases and monitor treatment. Furthermore, the concentration of haemoglobin, directly related to the number of erythrocytes, in the blood sample is also of great importance.

Thus, much effort has over the years been devoted to the development of automated blood cell counting systems. For the sake of completeness, manual counting using microscope techniques of blood cells using smears of blood samples should also be mentioned here. The latter techniques are, however, time-consuming and require relatively high level of training by the performer. Automated blood cell counting systems can be divided into two major groups: those relying on the impedance cell sizing principle (equal to the Coulter principle) and those relying on the flow cytometry principle. Examples of such automated systems are Coulter AcT Diff based on impedance cell sizing and Bayer ADVIA 120 based on flow cytometry. Both principles can be combined with spectrophotometric techniques for additional analysis of soluble components in the blood, such as haemoglobin.

The automated blood cell counting systems analyse the number of erythrocytes and thrombocytes simultaneously using a special procedure involving dilution of the blood sample with cell-preserving reagent. The number of leukocytes are on the other hand separately analysed by exposing the blood sample to a lysing reagent containing compounds capable of lysing the erythrocytes since they interfere with the enumeration of the leukocytes. The interference, not using erythrocyte-lysing compounds, is due to the overlap in cell size and it is thus not possible to count the leukocytes in the presence of the erythrocytes by size discrimination alone.

The lysing reagent does also affect the leukocytes but only to such an extent that these can still be enumerated. As a consequence of lysing the erythrocytes, the haemoglobin is released and can thus be properly analysed using spectrophotometric techniques. A great number of (erythrocyte) lysing reagents mixtures have been developed. In these mixtures specific compounds, surfactants, are responsible for the lysing action. Examples of such compounds are quaternary ammonium salts as described in U.S. Pat. No. 4,485,175, U.S. Pat. No. 4,346,018, U.S. Pat. No. 4,745,071, U.S. Pat. No. 4,528,274, U.S. Pat. No. 5,763,280, U.S. Pat. No. 5,834,315 and saponins as described in U.S. Pat. No. 4,751,179, U.S. Pat. No. 5,731,206, U.S. Pat. No. 5,840,515, U.S. Pat. No. 5,348,859, EP 0549 414 B1. Different lysing reagent in the automatic blood cell counting systems as described above have different effect on the system to enumerate the three leukocyte subpopulations: lymphocytes, monocytes and granulocytes. In order to also be able to enumerate the three granulocytes sub-populations: eososinophils, basofis and neutrophils the lysing reagent also contains specific compounds rendering these three subpopulations different properties. As an alternative these three granulocytes subpopulations can be enumerated using complementary radio frequency analysis contained in the automated blood cell counting systems based on the impedance cell sizing principle.

In EP 0549 414 B1, a process is disclosed wherein a combined enumeration of erythrocytes and thrombocytes in a blood sample is performed followed by addition of an erythrocyte lysing agent whereafter the remaining thrombocytes are enumerated again. Finally, the number of the erythrocytes and the thrombocytes, respectively, is calculated.

According to the present invention, an improved method and apparatus is provided for enumeration of different types of blood cells, such as different types of white blood cells, such as leukocytes, thrombocytes, etc, in blood. The method and apparatus involve counting and distinguishing the different types in one counting operation, e.g. in a flowcytometer, in a Coulter counter, etc. A lysing reagent is added to a blood sample for lysing of the erythrocytes. The composition of the lysing reagent is accurately controlled so that the required lysing is performed without deteriorating the cell types that it is desired to enumerate. For example, in a Coulter counter, the diameter of the orifice is optimised for counting of cell sizes corresponding to the cell sizes of the different types of cells it is desired to enumerate after lysing by the lysing reagent.

For example, the lysing reagent according to the present invention may be contained in a cartridge utilised in an apparatus for enumeration of cells in a blood sample, comprising a housing with a first mixing chamber and a first collection chamber separated by a wall containing an orifice for passage of the cells between the first mixing chamber and the first collection chamber. Cell characterization means are provided for characterizing cells passing through the orifice. The apparatus comprises a docking station for removably receiving the cartridge, the docking station comprising connectors for operational connection with the cell characterization means when the cartridge is received in the docking station.

With the electrical impedance technique of the Coulter counter principle, it is possible to resolve the cell volume from the measurement. By maintaining a constant current across the orifice, the recorded voltage pulse from cells displacing the electrolyte in the orifice will have a height proportional to the volume of the cell. This is because cells can be considered non-conducting compared to the electrolyte, the electrical field (DC or RF) in the centre of the orifice is homogeneous, which is normally the case when the diameter D is smaller than the length l of the orifice (l/D>1), the cell d is to be considered small compared to the diameter of the orifice (d<0.2*D), only one cell passes through at a time and the cells are passed through the orifice along the length or depth of the orifice.

Preferably, the length of the orifice is from 1 to 1000 µm, for example about 50 µm. Desirably the length of the orifice is chosen such that only one cell will be present in the orifice at the time when detecting cells of from 0.1 to 100 µm diameter. However, considerations to the homogeneity of the electrical field in the orifice may require a length of the orifice larger or equal to the diameter. The counts, of which some may be simultaneous counting of two cells, can be corrected mathematically by implementing a statistical estimation. The aspect ratio of the orifice, (length or depth divided by diameter) is preferably from 0.5:1 to 5:1, more preferably from 1:1 to 3:1.

Preferably, the largest cross-sectional dimension of the orifice is from 5 to 200 µm, for example 10 to 50 µm.

As a supplement a spectrophotometric measurement can be performed in order to quantify the content of e.g. haemoglobin.

The lysing reagent according to the present invention affects various types of blood cells. For example, the erythrocytes are completely eliminated, the leukocytes decrease in volume and the thrombocytes also decrease in volume. However, the composition of the lysing reagent is accurately controlled so that the decrease in volume of the thrombocytes is not significant for the ability of the thrombocytes to be counted in a Coulter counter. It has been verified that the identified parts of the remains of the thrombocytes were related to the original content of thrombocytes in the blood samples according to comparative methods. This is further described below.

The different behaviour of the different blood cells when exposed to the lysing reagent in question, can be explained taken the different structures of the three types of blood cells, as outlined above, into account and its consequence on the remains of these after exposure to the lysing reagent. The remains of the leukocytes are made up of the granula possibly surrounded by a collapsed cell membrane and/or a decreased amount of cytoplasm. The erythrocyte cell membrane disintegrates completely during the action of the lysing reagent. Since the erythrocytes do not contain any cell organelles, small cell membrane debris is the only remains of this blood cell type. This debris is difficult to separate from the background-noise of automatic blood cell counting systems based on the impedance cell sizing. The remains of the thrombocytes after exposure to the lysing reagent could be made up of cell organelles possibly surrounded by a collapsed cell membrane after complete disintegration of the outer surface coat.

In order to further separate the remains of the thrombocytes from the background-noise we found that use of an automatic blood cell system, based on impedance cell sizing principle, with a smaller orifice can be made. Using an orifice with a diameter of 50 µm, 5% of the thrombocytes present in the sample can thus be accounted for. This part of the thrombocytes can be increased up to 49% using an orifice with a diameter of 44 µm. Finally, using an orifice with a diameter of 40 µm, 63% of the in the sample present thrombocytes can be accounted for.

The cartridge may comprise the following parts:
1. A liquid storage chamber
2. A blood-sampling device
3. A first mixing chamber
4. A flow through sensor arrangement
5. A first collection chamber
6. A volume metering arrangement comprised of a chamber and two connected flow channels
7. A hydraulic connection for moving the liquid through the cartridge The concept of the disposable unit can be further combined with the following additional parts:
A. Optical structures for optical liquid level measurement
B. Electrodes for liquid level measurement
C. Anti-coagulation treatment of surfaces
D. Reagents in the diluent for modification of e.g. blood cells
E. Mixing flee or baffle for assisted mixing
F. Multiple volume metering arrangements for altering volumes
G. A coating tape covering the sample inlet before use
H. A waste chamber for waste/overflow
I. A valve preventing liquid to exit through exhaust tube
J. A piston or membrane instead of the vacuum tube
K. A window for spectrophotometric measurements The liquid storage chamber (part 1) holds the required amount of diluent used for the blood analysis. When the blood has been sampled into the cartridge, the diluent is flushed through the capillary to wash out the sampled blood and dilute it as required by the test. Dilutions of 100 to 100,000 times are considered to be normal ratings and dilutions of 500 to 10,000 times are preferred. The liquid storage chamber should preferably be constructed to facilitate total draining of the chamber. This would be accomplished by having a slanting of the bottom of the chamber.

The sampling unit (part 2) may comprise a capillary extending through a movable rod placed in a tight-fitting supporting body. The movable rod is used for entrapment of a precise amount of blood sample. When blood has filled the capillary by capillary forces, the rod is turned and/or displaced from its initial position in the supporting body, thus isolating the part of the capillary that extends through the rod.

After moving the rod in the supporting body into its second position the capillary forms a liquid path between the liquid storage chamber and the first mixing chamber (part 3). By applying a low pressure to the first mixing chamber the diluent and blood sample is forced into the first mixing chamber, where mixing will be performed by convection or subsequently by blowing bubbles into the mixing chamber.

The flow through sensor arrangement (part 4) is comprised of a small orifice in a membrane that establishes a liquid path from the first mixing chamber to the first collection chamber. On each side of the membrane (in the first mixing chamber and in the first collection chamber) an electrode is placed contacting the liquid.

The first collection chamber (part 5) forms a liquid priming function of the backside of the sensor system.

The volume metering system (part 6) is necessary for determination of the cell concentration. It comprises volume-metering chamber of a known volume with two relatively thin channels connecting the inlet at the bottom and the outlet at the top. Sensing of the liquid at the inlet and outlet can be applied by optical or electrical means.

The outlet of the volume metering system is connected through a channel (part 7) to a source of pressure for moving the liquid through the cartridge.

The additional parts to the concept are further described here:

Addition A: Optical detection by change of optical properties of a channel such as changed reflectance or transmittance due to replacement of air with liquid in the channel. The surface over the inlet and outlet of the volume-metering cell should be structured to optimize the coupling of the light into the channel. The presence of liquid in a transparent polymer channel will result in a transmission of the signals as opposed to a reflection when no liquid is present, which can be registered by optical sensors.

Addition B: Two electrodes for liquid level measurement are connected through the body of the cartridge into the inlet and outlet of the volume-metering cell respectively. The electrodes will be short-circuited through the saline liquid to the electrode placed in the first collection chamber, which can be registered through an external electrical arrangement.

Addition C: The anti-coagulation treatment of surfaces in the sampling structure can be achieved by having selected compounds adhered or chemically bonded to these surfaces. Examples of such compounds are heparin and salts of EDTA.

Addition D: Reagent in the diluent for modification of e.g. blood cells. This reagent can consist of one or several compounds capable of hemolysing the erythrocytes. In addition other compounds may be added in order to: stabilize leukocytes and/or thrombocytes, adjust the pH-value and osmotic pressure, minimize bacterial growth, modify the haemoglobin present and minimize batch to batch variations. The following examples have been included to provide information on relevant subjects related to the performance of a self-contained test cartridge.

Examples of compounds capable of selectively hemolysing the red blood cells are: mixtures of quaternary ammonium salts as described in e.g. U.S. Pat. No. 4,485,175; U.S. Pat. No. 4,346,018; U.S. Pat. No. 4,745,071; U.S. Pat. No. 4,528,274; and U.S. Pat. No. 5,834,315.

Examples of compounds capable of, during the hemolysis of the red blood cells, stabilizing the leukocytes are N-(1-acetamido)iminodiacetic acid, procaine hydrochloride as described in e.g. U.S. Pat. No. 4,485,175 and 1,3-dimethylurea as described in e.g. U.S. Pat. No. 4,745,071. In addition N-(1-acetamido)iminodiacetic acid is proposed to further assist the quaternary ammonium salts in minimizing debris stemming from hemolysed red blood cells as described in e.g. U.S. Pat. No. 4,962,038 and adjust the pH-value (see below).

Examples of compounds added in order to adjust the pH-value and not least importantly the osmotic pressure of the diluent are: N-(1-acetamido)iminodiacetic acid, sodium chloride, sodium sulphate as described in e.g. U.S. Pat. No. 4,485,175 and U.S. Pat. No. 4,962,038.

Examples of compounds capable of minimizing bacterial growth are: 1,3-dimethylolurea and chlorhexidine diacetate as described in e.g. U.S. Pat. No. 4,962,038.

Examples of compounds added to convert the haemoglobin species to an end-product suitable for spectrophotometric analysis are: potassium cyanide as described in e.g. U.S. Pat. No. 4,485,175; U.S. Pat. No. 4,745,071; U.S. Pat. No. 4,528,274 and tetrazole or triazole as described in WO 99/49319.

Examples of cells or compounds which may be added in order to introduce a tool for minimizing variation between different batches of the disposable device are: latex beads of known size and glass beads of known size.

Addition E: If assisted mixing is required the first mixing chamber might optionally include a mixing flee or a baffle. A magnetic flee may be used to force the convection through an externally moving magnetic field. A baffle may be used to mechanically stir the liquid when moved by an externally connecting mechanical device. This could be required if mixing with bubbles, such as bubbles blown into the sample through the sensor, is not adequate or possible.

Addition F: Multiple volume metering arrangements can be successively included if the test must deal with different concentrations of the different cells.

Addition G: A lid or coating tape may be used to cover the sample inlet before use. This ensures a clean sampling area at the origination of the test.

Addition H: A waste chamber may be applied at the outlet of the volume-metering cell for waste or overflow of liquid.

Addition I: At any connection ports, e.g. the connection port to the pressure source, a small valve can be integrated to prevent liquid to leak out of the cartridge.

Addition J: A piston or membrane can be integrated into the cartridge to include a source of pressure for moving the liquid. The piston or membrane could be moved by a mechanical force provided by the instrument.

Addition K: An optical window can be integrated into the cartridge in order to perform optical measurements such as spectrophotometric detection of the haemoglobin content in a blood sample.

The methods described can be combined to give the best solution for the final application. The disposable sensor is particularly usable where portable, cheap, simple or flexible equipment is needed, such as in small laboratories, in measurements in the field or as a "point of care" ("near-patient") diagnostic tool.

When using the Coulter principle the diluent for use in the apparatus according to the invention may contain inorganic salts rendering the liquid a high electrical conductivity. When sample is applied to the electrolyte, the electrolyte to sample volumes should preferably be higher than 10. Sample preparation should preferably result in between 1,000 to 10,000,000 cells per ml and more preferably between 10,000 and 100,000 cells per ml. A mixing of the sample after adding electrolyte is recommended. Cell diameters should preferably be within 1 to 60 percent of the orifice diameter and more preferably between 5 to 25 percent of the orifice diameter. Volume flow should preferably be from 10 µl to 10 ml per minute and more preferably between 100 µl and 1 ml per minute. For the measurement a constant electrical current of approximately 1 to 5 mA should preferably be applied. The source of electrical current should preferably have a signal to noise ratio (S/N) better than 1,000. The response from the electrodes can be filtered electronically by a band-pass filter.

According to yet another aspect of the invention a cartridge is provided comprising a housing with a first mixing chamber and a first collection chamber separated by a wall containing a first orifice for the passage of the cells between the first mixing chamber and the first collection chamber, first cell characterization means for characterizing cells passing through the first orifice, a bore in the outer surface of the housing for entrance of the blood sample, communicating with a first sampling member positioned in the housing for sampling the blood sample and having a first cavity for receiving and holding the blood sample, the member being movably positioned in relation to the housing in such a way that, in a first position, the first cavity is in communication with the bore for entrance of the blood sample into the first cavity, and, in a second position, the first cavity is in communication with the first mixing chamber for discharge of the blood sample into the first mixing chamber.

The cartridge may further comprise a second mixing chamber and a second collection chamber separated by a second wall containing a second orifice for the passage of the cells between the second mixing chamber and the second collection chamber, second cell characterization means for characterizing cells passing through the second orifice.

In one embodiment of the invention, the first cavity is in communication with the first mixing chamber, when the first sampling member is in its first position, for entrance of liquid from the first mixing chamber into the first cavity, and, in a third position of the first sampling member, the first cavity is in communication with the second mixing chamber for discharge of the liquid in the first cavity into the second mixing chamber.

In another embodiment of the invention, the cartridge further comprises a second sampling member positioned in the housing for sampling a small and precise volume of liquid from the first mixing chamber and having a second cavity for receiving and holding the sampled liquid, the member being movably positioned in relation to the housing in such a way that, in a first position, the second cavity is in communication with the first mixing chamber for entrance of liquid from the first mixing chamber into the first cavity, and, in a second position, the second cavity is in communication with the second mixing chamber for discharge of the sampled liquid in the second cavity into the second mixing chamber.

The cartridge may further comprise a reagent chamber positioned adjacent to the first mixing chamber for holding a reagent to be entered into the first mixing chamber.

Preferably, the cartridge further comprises a breakable seal separating the reagent chamber from the first mixing chamber.

With this embodiment, different chemical treatment of different parts of the blood sample may be performed.

Figure 2:
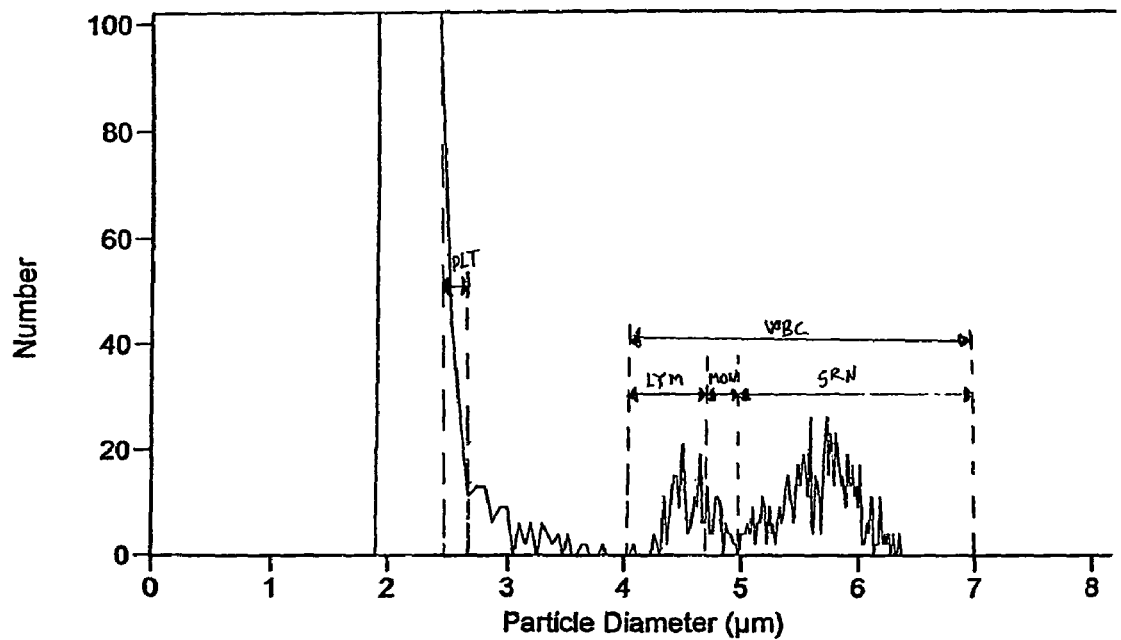
Figure 3:
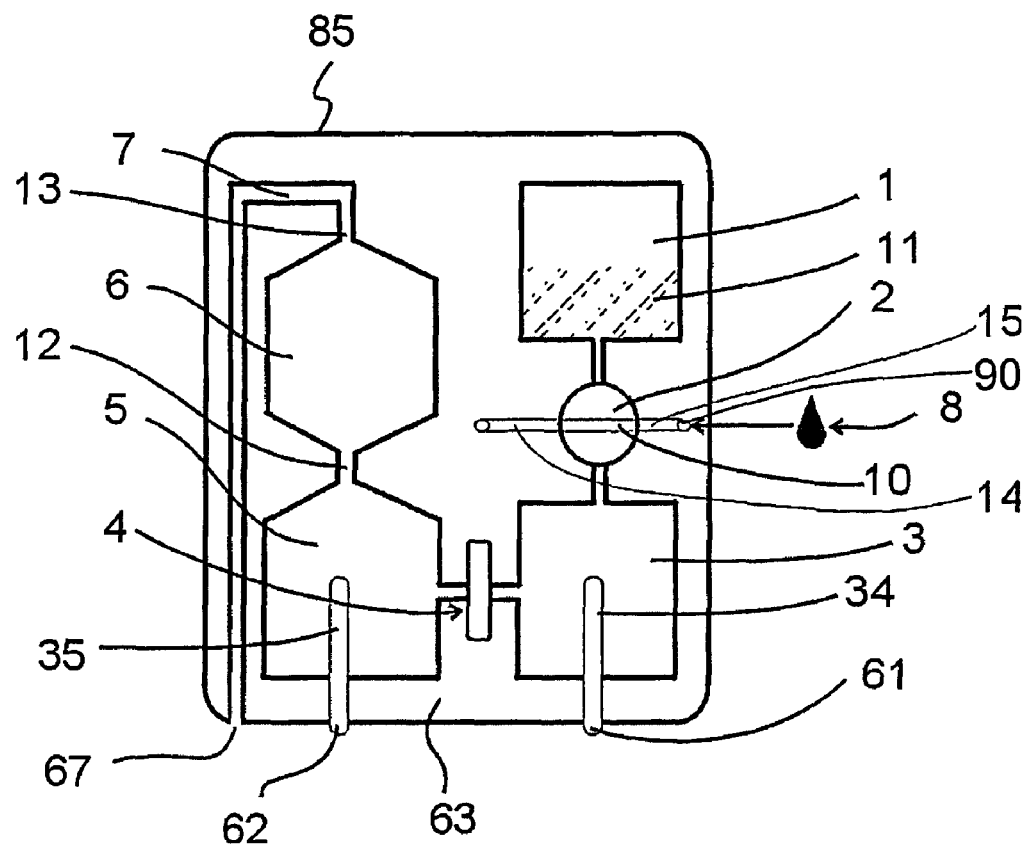
Figure 4:
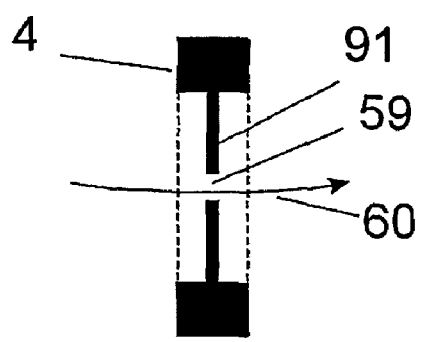
Figure 5:
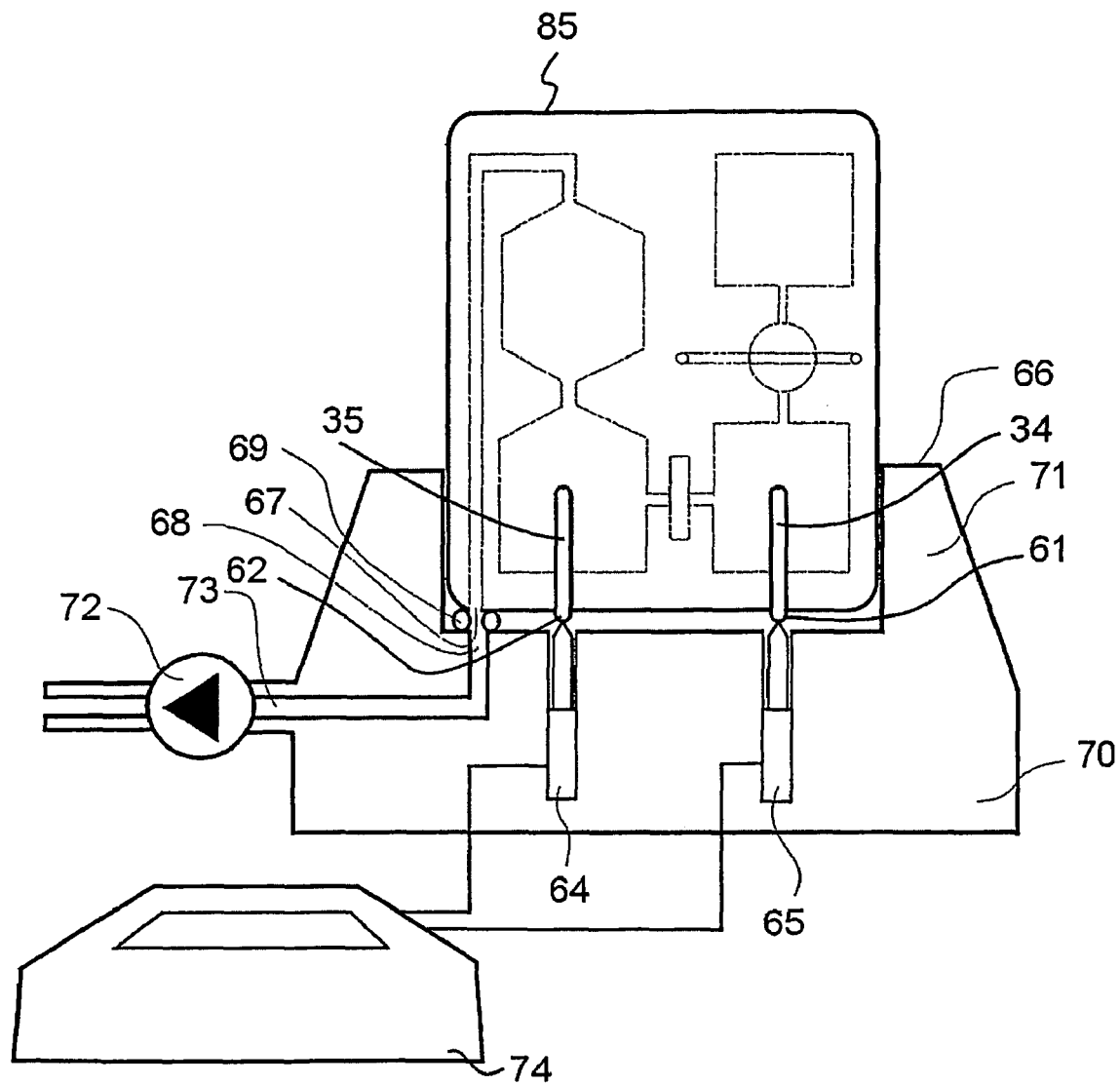
Figure 6:
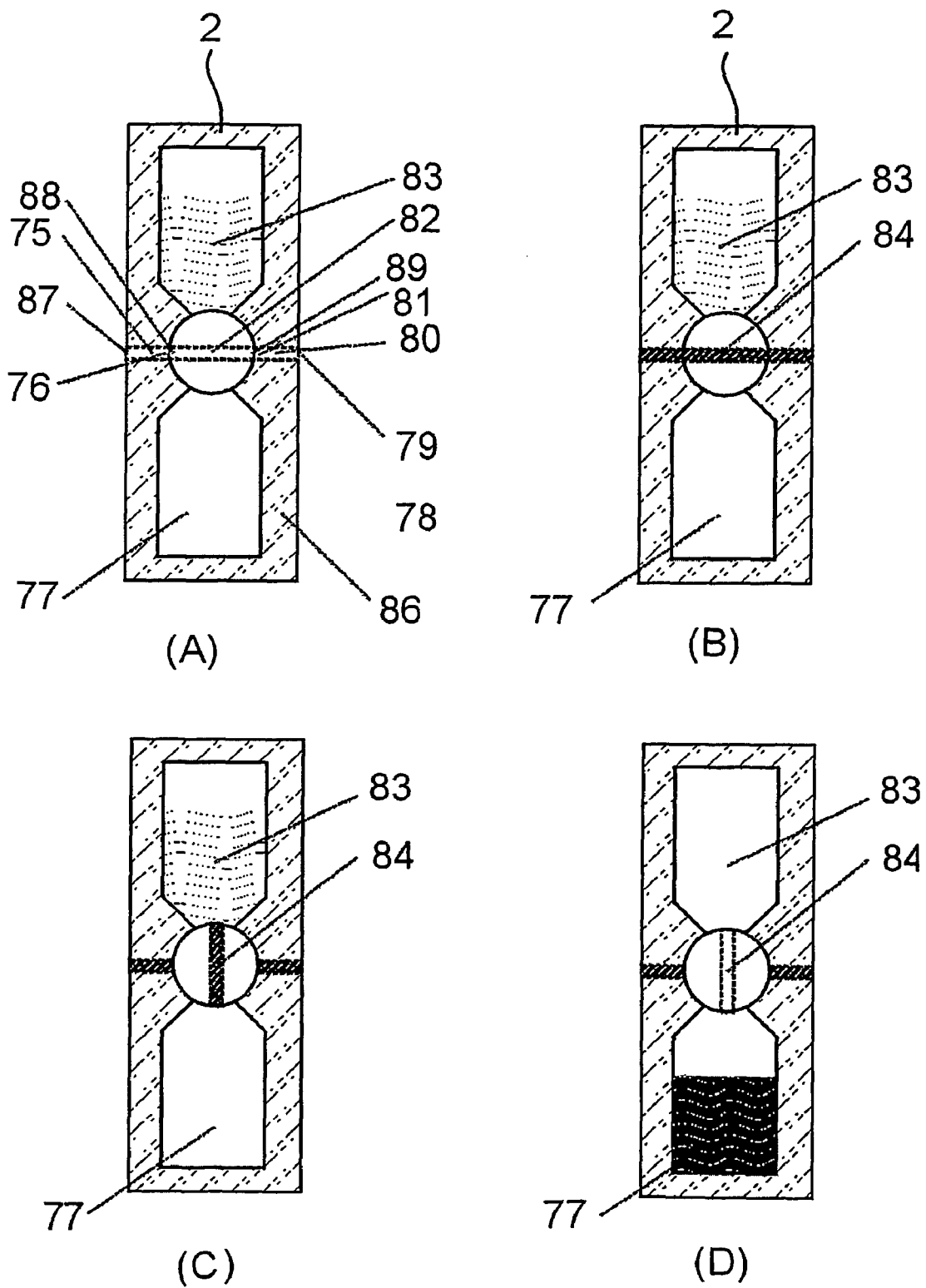
Figure 7:
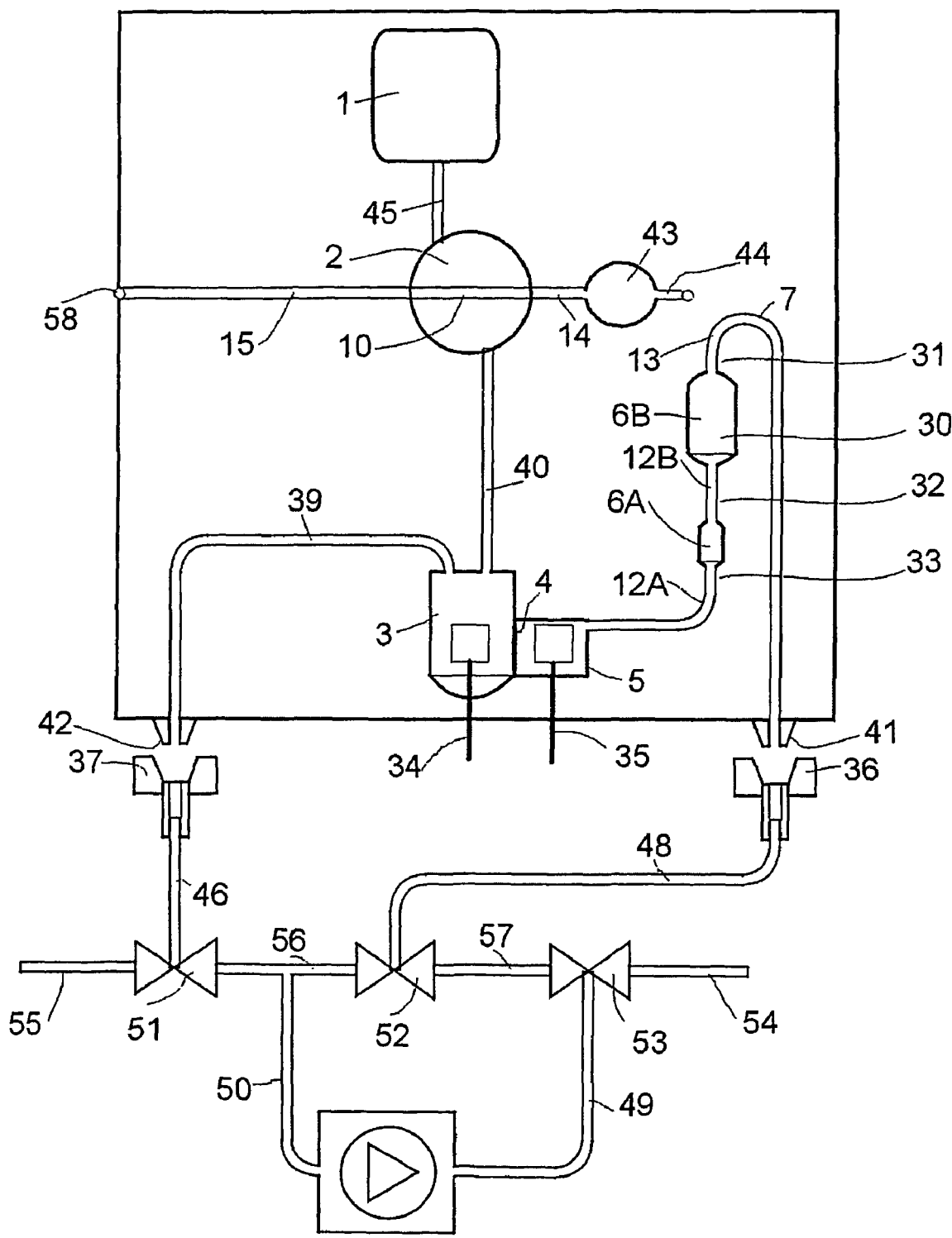
Figure 8:
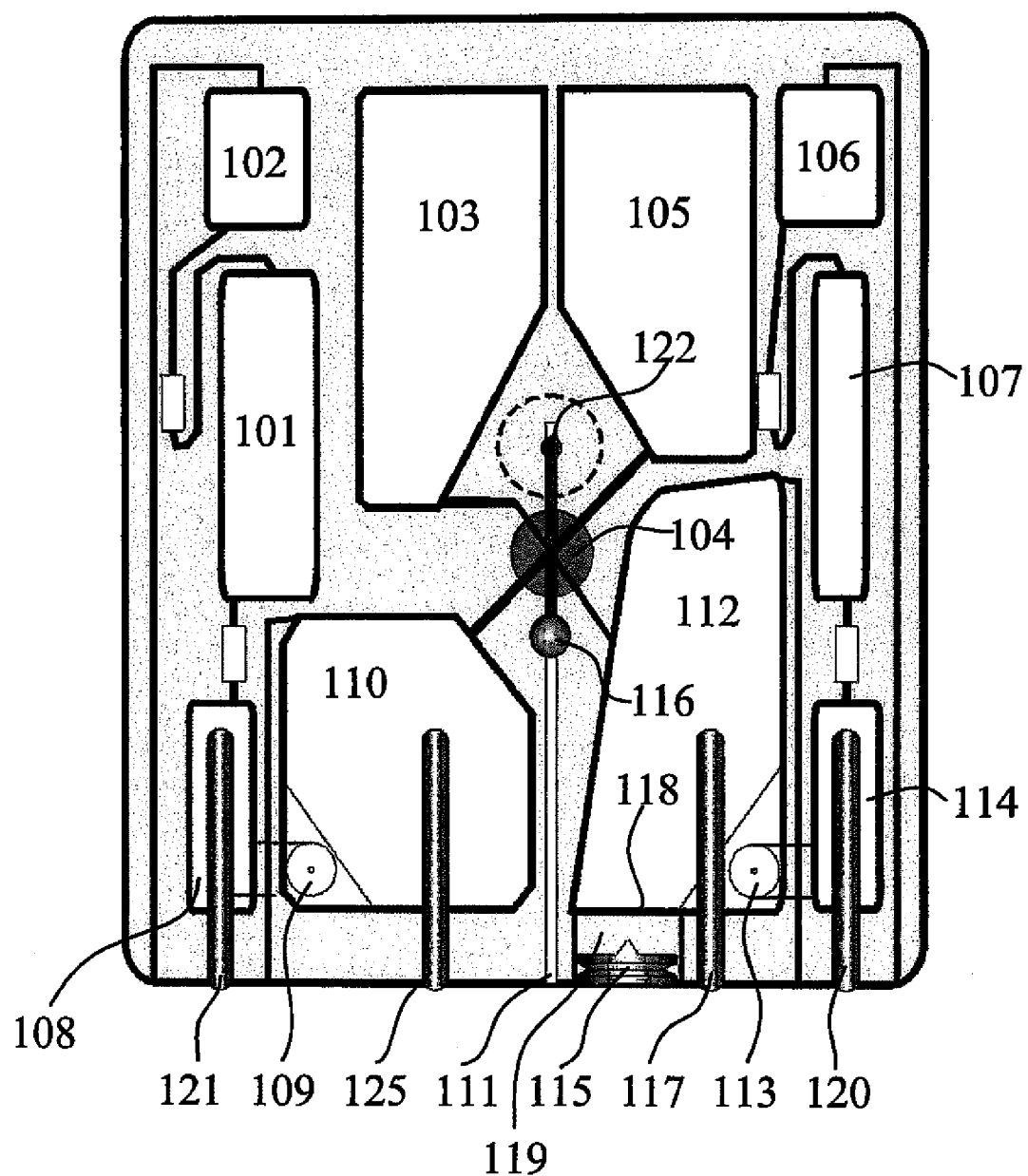
Figure 9:
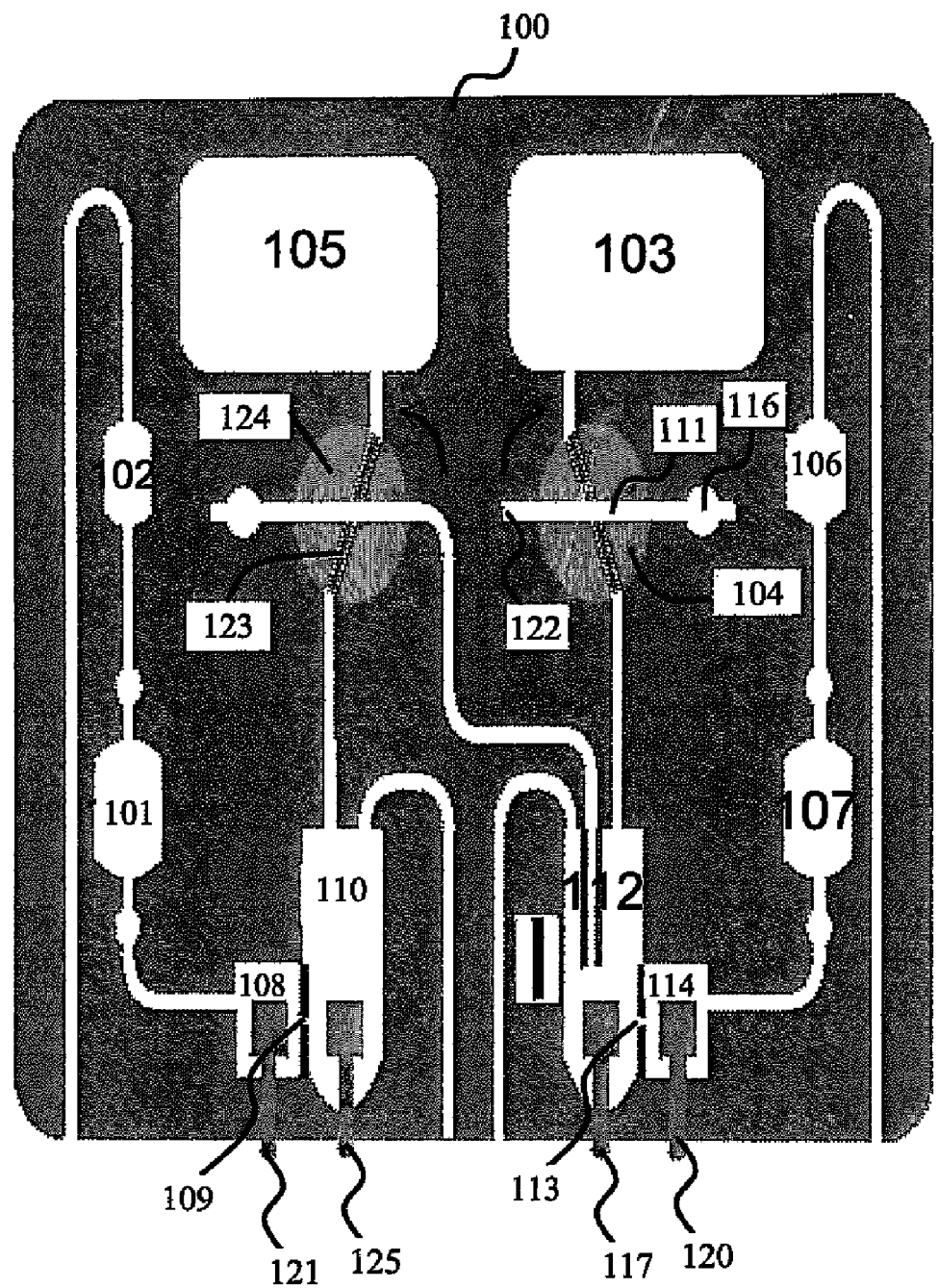
Figure 10:
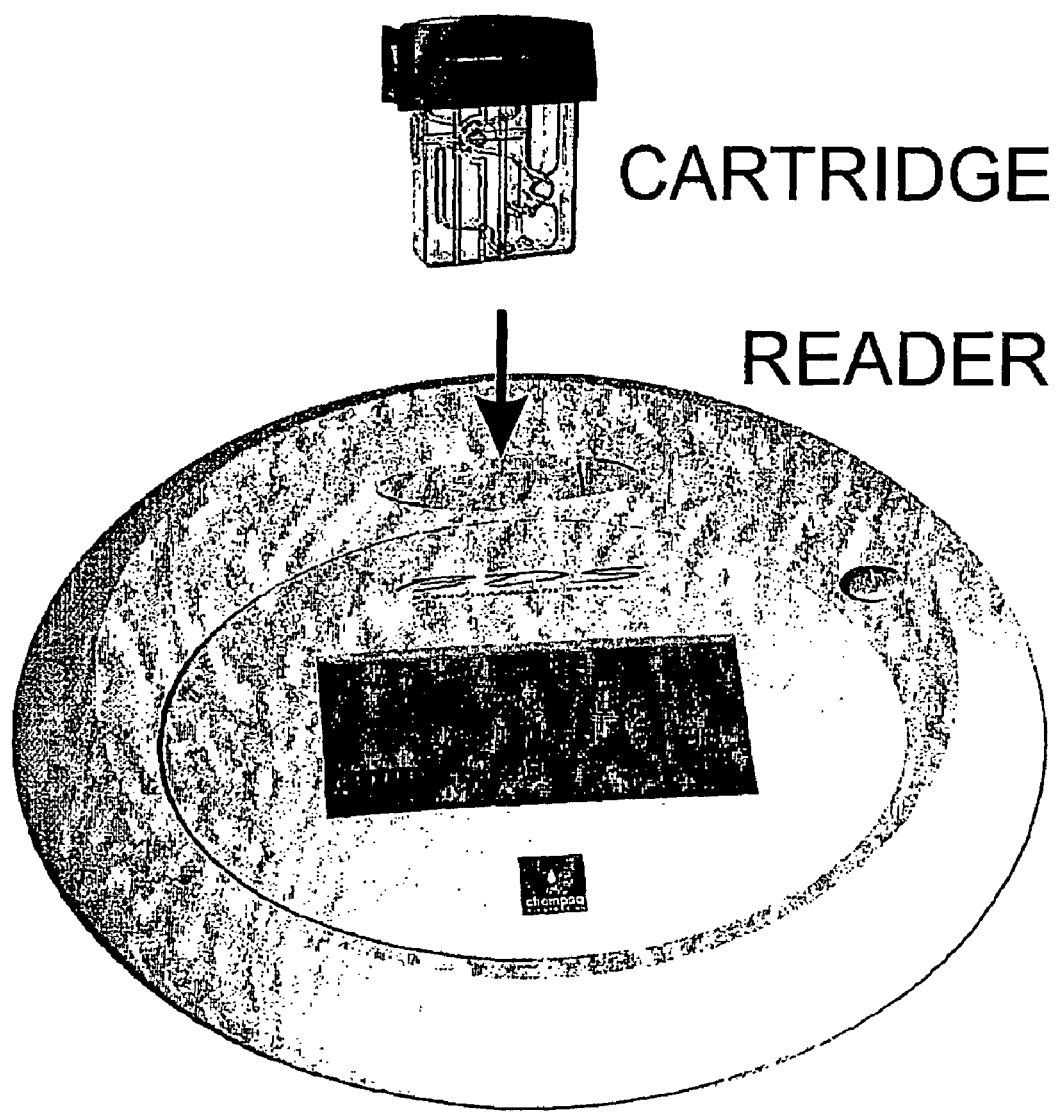

Also with this embodiment, further dilution of the blood sample may be performed. The invention will be further described and illustrated with reference to the accompanying drawings in which:

FIG. 1 illustrates cell volume reduction after treatment by the lysing reagent according to the present invention, FIG. 2 is a histogram of cell sizes in a blood sample after treatment by the lysing reagent according to the present invention, FIG. 3 shows a cross sectional side view through the components of a disposable unit 85, referred to as the cartridge, FIG. 4 schematically illustrates the flow-through sensor concept FIG. 5 illustrates an apparatus with a disposable cartridge, a docking station, and a reader, FIG. 6 schematically illustrates the sampling procedure, FIG. 7 schematically illustrates the cartridge and hydraulic connections, FIG. 8 schematically illustrates a second embodiment of the cartridge, FIG. 9 schematically illustrates a third embodiment of the cartridge, and FIG. 10 shows in perspective an apparatus according to the invention.

The elimination of the erythrocytes and the decrease in volume of the leukocytes and thrombocytes after exposure to the lysing reagent is shown in FIGS. 1a (before lysing) and 1b (after lysing). Further, as can be seen in FIG. 2, the leukocytes decrease so as remains of them can be found in the particle size interval of 4-7 µm. This should be compared to their original diameter of 8 to 20 µm. Also, according to FIG. 2, the largest remains of the thrombocytes have a diameter of 2.5 µm, which should be compared to their original range in diameter of 2 to 4 µm (ref. M. L. Stevens, Fundamentals of Clinical Haematology, W.B. Saunders Company, 1997).

EXAMPLE 1

Counting of thrombocytes, leukocytes, lymphocytes, monocytes and granulocytes.

Use of a reagent mixture containing quaternary ammonium salts.

Material 3 fresh venous blood samples in ($K_3$)EDTA-collection tubes.

Coulter Particle Size and Particle Counter Z-2 equipped with a 50 µm orifice.

Lysing reagent mixture: 0.450 g 1,2,4-Triazole, 0.178 g Dodecyltrimethylammonium chloride and 0.038 g Hexadecyltrimethylammonium bromide were dissolved in 90 ml Diluide III-Diff (J. T. Baker). To this solution 28.9 ml of de-ionised water was added. The final solution was filtered (0.22 µm).

Methods

The samples were first analysed for comparative purposes using an ADVIA-120 (Bayer) system. Thereafter the blood samples were diluted 500 times by adding 20 µl of them to 9.980 ml of lysing reagent mixture. Finally they were analysed on the Coulter Particle Size and Particle Counter within 2 minutes after dilution.

Results

FIG. 2. shows a histogram for analysis of one of the blood samples. In this histogram the ranges used for correlation to the remains of the different blood cells are shown. Identical ranges were used in the analogous analysis of the remaining two blood samples.

TABLE 1

| Blood sample | Analyte | Obtained result | Comparative result | Deviation# |
|---|---|---|---|---|
| 1 | Thrombocytes | 391 × 10e9 | 351 × 10e9 | 11 |
| 2 | Thrombocytes | 343 × 10e9 | 359 × 10e9 | −4.4 |
| 3 | Thrombocytes | 340 × 10e9 | 300 × 10e9 | 13 |
| 1 | Leukocytes | 5.21 × 10e9 | 5.42 × 10e9 | −4.0 |
| 2 | Leukocytes | 4.36 × 10e9 | 4.24 × 10e9 | 2.8 |
| 3 | Leukocytes | 5.33 × 10e9 | 5.35 × 10e9 | −0.5 |
| 1 | Lymphocytes | 1.23 × 10e9 | 1.19 × 10e9 | 3.5 |
| 2 | Lymphocytes | 0.44 × 10e9 | 0.41 × 10e9 | 8.4 |
| 3 | Lymphocytes | 1.03 × 10e9 | 1.14 × 10e9 | −9.8 |
| 1 | Monocytes | 0.27 × 10e9 | 0.30 × 10e9 | −10 |
| 2 | Monocytes | 0.16 × 10e9 | 0.14 × 10e9 | 15.7 |
| 3 | Monocytes | 0.36 × 10e9 | 0.40 × 10e9 | −10 |
| 1 | Granulocytes | 4.09 × 10e9 | 3.94 × 10e9 | 3.7 |
| 2 | Granulocytes | 3.92 × 10e9 | 3.69 × 10e9 | 6.2 |
| 3 | Granulocytes | 4.32 × 10e9 | 3.80 × 10e9 | 14 |

100 × (Obtained result − Comparative result)/Comparative result

EXAMPLE 2

Counting of thrombocytes, leukocytes, lymphocytes, monocytes and granulocytes.

Use of a reagent mixture containing saponin.

Material

Two fresh venous blood samples in ($K_3$)EDTA-collection tubes.

Coulter Particle Size and Particle Counter Z-2 equipped with a 50 µm orifice.

Lysing reagent mixture: 2.063 g of Saponin (ACROS, prod. no. 41923100) was dissolved in 500 ml Diluide III-Diff (J. T. Baker). The final solution was filtered (0.22 μm).

Methods

The samples were first analysed for comparative purposes using an ADVIA-120 (Bayer) system. Thereafter the blood samples were diluted 500 times by adding 20 μl of them to 9.980 ml of lysing reagent mixture. Finally they were analysed on the Coulter Particle Size and Particle Counter within 2 minutes after dilution.

Results

Identical ranges in the histogram (compare FIG. 2) were used in the analogous analysis of the two blood samples.

TABLE 2

| Blood sample | Analyte | Obtained result | Comparative result | Deviation# |
|---|---|---|---|---|
| 1 | Thrombocytes | 189 × 10e9 | 190 × 10e9 | −0.5 |
| 2 | Thrombocytes | 284 × 10e9 | 283 × 10e9 | 0.4 |
| 1 | Leukocytes | 5.41 × 10e9 | 5.12 × 10e9 | 5.6 |
| 2 | Leukocytes | 7.64 × 10e9 | 6.77 × 10e9 | 13 |
| 1 | Lymphocytes | 1.76 × 10e9 | 1.77 × 10e9 | −0.8 |
| 2 | Lymphocytes | 1.64 × 10e9 | 1.64 × 10e9 | 0 |
| 1 | Monocytes | 0.25 × 10e9 | 0.24 × 10e9 | 4.2 |
| 2 | Monocytes | 0.22 × 10e9 | 0.26 × 10e9 | −15 |
| 1 | Granulocytes | 3.28 × 10e9 | 3.11 × 10e9 | 5.3 |
| 2 | Granulocytes | 5.47 × 10e9 | 4.88 × 10e9 | 12 |

100 × (Obtained result − Comparative result)/Comparative result

FIG. 3 schematically illustrates a disposable cartridge with a housing 85 for blood analysis comprises a liquid storage chamber 1 containing a liquid diluent 11, a first sampling member 2 positioned in the housing 85 for sampling a blood sample 8 and having a cavity 10 for receiving and holding the blood sample 8, the member 2 being movably positioned in relation to the housing 85 in such a way that, in a first position, the cavity 10 is in communication with a bore 90 for entrance of the blood sample 8 into the cavity 10 by capillary forces, and, in a second position, the cavity 10 is in communication with the liquid storage chamber 1 and a mixing chamber 3 for discharge of the blood sample 8 diluted by the liquid diluent 11 into the mixing chamber 3. The mixing chamber 3 is separated by a wall containing an orifice 59 from and a collection chamber 5 for the passage of the blood sample 8 between the mixing chamber 3 and the collection chamber 5. The wall containing the orifice 59 constitutes a part of a flow-through sensor 4.

A volume metering arrangement is connected to the collection chamber comprising a volume metering chamber 6 having the size of the volume to be measured during the measurement with two connecting channels 12, 13 of relatively diminutive internal volumes for registering liquid entry and exit by optical or electrical means, from the volume metering chamber a channel 7 leads out to a connection port 67 where a pressure can be applied.

FIG. 4 schematically illustrates, the flow-through sensor 4 has a dividing wall 91 with a relatively thin passage 59 for the passage of cells suspended in liquid. The passage serves as a sensing zone for detection and measurement of the individual cells. The passage in the sensor may be formed as a count orifice for counting and sizing cells by an impedance method known as Coulter counting. Cells can be aspirated through the orifice by pressure driven flow in either direction. When a saline or other electrolytic liquid solution is added to the chambers, the two chambers will be electrically isolated from each other except for the route for current flow provided by the passage through the orifice.

FIG. 5 illustrates an apparatus with a disposable cartridge, a docking station, and a reader. The chambers on each side of the flow through sensor have electrodes 34, 35 extending from an external terminal 61, 62 through the base wall 63 of the disposable unit and into a configuration facing the inside of its respective chamber. The cartridge is placed in a docking station 66 in a portable apparatus in order to carry out the test. The docking station 66 has a cup shaped housing having a base 70 and a circumambient sidewall 71. In the base 70 there are respective spring loaded electrical connectors 64, 65 for contacting the terminals 61, 62 of the cartridge automatically when the cartridge is received as a push fit into the docking station. There is also a conduit 68 passing through the base wall 70 aligned with the conduit 67 of the cartridge. Conduit 67 at its opening into the upper face of the wall 70 has a seal 69, such as e.g. and O-ring for forming a gas tight connection with the lower face of the base wall 63 of the cartridge. A vacuum pump 72 is connected by a line 73 to the lower end of the conduit 68. In a modification of the apparatus, the vacuum pump 72 can be reversed so as to apply positive gas pressure to the conduit 68. Schematically indicated at 74 are the further conventional components of a Coulter counter including all the electronic circuitry and display equipment needed for the operation of the apparatus.

FIG. 6 schematically illustrates the blood sampling operation. The illustrated part of the cartridge 2 includes the liquid storage chamber 83 for storing a diluent for diluting the sample and the first mixing chamber 77 for mixing the sample 84 and the diluent. This figure schematically illustrates a device for sampling a small and accurate volume of liquid in accordance with the present invention. The device 10 comprises a first member 86 with a first opening 87 for entrance of a blood sample into a bore 75 in the first member 86 and with a second opening 76 for outputting the blood sample from the bore 75. The bore 75 forms a capillary tunnel. The first opening 87 of the first member 86 may be brought into contact with a liquid 8 (shown in FIG. 3), 84 to be sampled so that the liquid 84 may flow through the first opening 87 into the bore 75 and out of the second opening 76 by capillary attraction. The device 12 further comprises a sampling member 78 with a first cavity 82 for receiving and holding the blood sample 84 and having a third opening 88 communicating with the first cavity 82. The first cavity forms a capillary tunnel with essentially the same diameter as the bore 75. The sampling member 78 is a circular cylinder that is movably positioned in relation to the first member 86. During sampling of the liquid, the sampling member 78 is positioned in the illustrated first position in relation to the first member 86 wherein the second opening 76 is in communication with the third opening 88 so that sampled liquid may flow through the second 76 and third opening 88 into the first cavity 82 by capillary attraction. The third opening 88 may be disconnected from the second opening 76 in a second position of the sampling member 78 in relation to the first member 86 so that the blood sample 84 contained in the first cavity 82 is disconnected from the bore 75.

The sampling member 78 is inserted into a third cavity 34 of the first member 86 for receiving and accommodating a part of the sampling member 78. The sampling member 78 may be displaced between the first and second position along a longitudinal axis of the sampling member 78 that is also substantially perpendicular to a longitudinal axis of the first cavity 82. The sampling member 78 may also be rotatable about a longitudinal axis that is substantially perpendicular to a longitudinal axis of the first cavity 82. In the first position, the first 75 and second 82 capillary tunnels extend along substantially the same longitudinal centre axis.

In the illustrated embodiment the first member 86 is symmetrical and has a fourth cavity 80 with openings 81, 79 opposite the bore 75, and the sampling member 78 has an opening 89 opposite the opening 88 so that, in the first position, a capillary tunnel extends through the first 86 and the second 78 member and communicates with the environment through openings 87, 79. Thus, air may escape from the capillary tunnel through opening 79. Further, in the first position, a part of the liquid entering the first cavity 82 will leave the cavity 82 through opening 89 thereby ensuring that the cavity 82 has been completely filled with liquid during liquid sampling eliminating the risk of sampling with a reduced sample volume leading to low accuracy sampling.

FIG. 6a illustrates the device 2 ready for receiving the liquid. In FIG. 6b, a sample has entered into the capillary tunnel 82, and in FIG. 6c the sampling member 78 has been rotated into the second position for isolation of an accurate volume of the sample 84, and finally FIG. 6d illustrates that the sample 84 has been washed out of the capillary tunnel 82 and into the first mixing chamber 77 by the diluent.

Example: The capillary tunnel forming the first cavity 82 may have a length of 8 mm and a diameter of 0.9 mm for containing a blood sample of 5.089 µL.

Example: The capillary tunnel forming the first cavity 82 may have a length of 5 mm and a diameter of 0.5 mm for containing a blood sample of 0.982 µL.

Example: The capillary tunnel forming the first cavity 82 may have a length of 3 mm and a diameter of 0.3 mm for containing a blood sample of 0.212 µL.

FIG. 7 schematically illustrates an apparatus with a disposable cartridge holding a lysing reagent according to the present invention, a docking station, and a reader. In the following the operation of the apparatus for counting different types of white blood cells, namely monocytes, lymphocytes, granulocytes, and thrombocytes and for determining haemoglobin content is explained.

The lysing reagent for selectively lysing red blood cells is added to the diluent in the storage chamber 1. When the whole blood 8 is added to the opening 58 of the first capillary section 15, the blood will be dragged in to the capillary and through the middle section 10 and last section 14 of the capillary. The last section of the capillary is connected to a fill-chamber 43 for visually verification of the filling. The fill-chamber 43 is connected through a conduct 44 to open air.

The blood filled middle section of the capillary is part of a knob 2 that can be moved to a second position, connecting the ends of the capillary to two other conducts, a conduct 45 connected to the storage chamber 1 and a second conduct 40 connected to the first mixing chamber 3 respectively. A third conduct 39 is leading from the first mixing chamber to a port opening 42 in the cartridge. The port opening is connected through a counter port opening 37 in the apparatus, through tubing 46 to a three-position valve 51 and directed through the two positions of the valve to open air through second tubing 55 or through a third tubing 50 to the suction port of a membrane pump 47.

When the blood and diluent with reagent has been sucked into the first mixing chamber, the blood can be mixed by blowing bubbles through the orifice of the sensor 4. The air pressure is applied through the collection chamber 5, via a fourth conduct 12A, a small volume chamber 6A, a fifth conduct 12B, a large volume chamber 6B and a sixth conduct 7 directed to an opening port 41 in the cartridge. A counter port 36 in the apparatus is connected through a fourth tubing 48 to a second three position valve 52, which has positions to direct to both vacuum through a fifth tubing 56 to the suction port of the membrane pump, or to the exhaust of the membrane pump, through a third two position valve 53 and a sixth tubing 49, the third valve having two positions for the connection and for directing the pump exhaust to open air through a seventh tubing 54 respectively.

After mixing the diluted and lysed blood (red blood cells is removed) it is ready to be measured. The first mixing chamber is connected through the first valve to open air and the collection chamber is connected through the second valve to the suction port of the pump. The exhaust of the membrane pump is connected through the third valve to open air. As the blood and diluent flows from the mixing chamber into the collection chamber, an electrical connection between to counter electrodes 34 and 35 placed in each chamber is established through the liquid. Cells are counted and differentiated by size according to the Coulter principle. Through sizing of the cells, the cells can be distinguished and categorised into different groups containing cells of a certain type. Thus, leucocytes can be differentiated into granulocytes, lymphocytes and monocytes. Furthermore, thrombocytes (platelets) can be differentiated from leucocytes as well. In order to determine the concentration, the volume of the diluted blood, which has been counted, must be known. Since thrombocytes are approximately ten times as frequent as leucocytes, it may be necessary to measure two different volumes. The thrombocytes are counted according to a small volume chamber 6A positioned between the collection chamber and the larger volume. By registering the liquid entry and exit at the inlet and outlet of the small volume chamber respectively, the counting period will be given. Registration of the liquid level is preferably done by an optical reflectance measurement at the inlet 33 and at the outlet 32. The outlet of the small volume chamber is also the inlet of the large volume chamber 6B. This chamber is used in connection with counting of leucocytes. At the outlet of the large volume chamber, a third optical reflectance measurement 31 is performed to register the exit of the liquid from this chamber.

After counting both leucocytes and thrombocytes the haemoglobin content can be measured by optical spectroscopy preferably through the middle section of the large volume chamber 30.

The process of making a test by means of the present invention can be characterized as:
1) Draw blood by using a lancet device
2) Pick up blood droplet by touching the blood to the cartridge inlet
3) Mount cartridge in the instrument (instrument starts and runs the test)
4) Read the result from the display
5) Remove and discard cartridge FIG. 8 shows schematically another preferred embodiment of the cartridge according to the invention. The illustrated cartridge has a first member 104 for sampling blood. The member 104 is movably positioned in relation to the housing 100 between three positions, a first position for blood sampling, a second position to connect the first storage chamber 103 with the first mixing chamber 112, and a third position to connect the second storage chamber 105 with the second mixing chamber 110. The blood is passed through the bore 122 into the first cavity of the member 104 by capillary forces or by applying a vacuum at the end of the sampling channel 111. A liquid blocking valve 116 is arranged after the first sampling member to hinder passage of blood through the channel. After the blood sampling, the sampling member is turned to the second position and the sample is flushed into the first mixing chamber 112 by the liquid in the first storage chamber 103. In the first mixing chamber 112 the sample is diluted 1:200 with the liquid in the first storage chamber 103 and a fraction is blown back into the first cavity of the sampling member 104, which is turned to the third position so that the diluted sample is flushed into the second mixing chamber 110 by the liquid in the second storage chamber 105. In the second mixing chamber 110 the sample is further diluted 1:200 to a total dilution of 1:40,000 with the liquid in the second storage chamber 105. A hemolysing reagent is injected into the first mixing chamber 112 by a piston 115, which breaks a seal 118 between a reagent chamber 119 and the first mixing chamber 112. After hemolysing the blood the 1:200 diluted sample is ready for counting non-hemolysed white blood cells and for measuring haemoglobin by photometry. The white cells are counted by passing them through a first orifice 113 and measuring the response by impedance cell counting over a first electrode pair 117, 120. A fixed volume is counted by a first volume metering arrangement 107 connected to the first collection chamber 114. A first overflow volume 106 is arranged after the first volume metering arrangement 107. The white blood cells can be differentiated by volume after adding the lysing reagent to the blood. The white cells can be grouped by volume into: Granulocytes, Monocytes and Lymphocytes. The three groups together yield the total white cell count.

In the second mixing chamber 11, red cells and platelets are counted. The red cells and platelets are counted by passing them through a second orifice 109 and measuring the response by impedance cell counting over a second electrode pair 121, 125. A fixed volume is counted by a second volume metering arrangement 101 connected to the second collection chamber 108. A second overflow volume 102 is placed after the second volume metering arrangement 101.

The embodiment may further comprise an additional optical detector for photometric determination of the haemoglobin content. Referred to simply as "total haemoglobin", this test involves lysing the erythrocytes, thus producing an evenly distributed solution of haemoglobin in the sample. The haemoglobin is chemically converted to the more stable and easily measured methemoglobintriazole-complex, which is a coloured compound that can be measured calorimetrically, its concentration being calculated from its amount of light absorption using Beer's Law. The method requires measurement of haemoglobin at approx. 540 nm where the absorption is high with a turbidity correction measurement at 880 nm where the absorption is low.

FIG. 9 shows schematically another preferred embodiment of the cartridge according to the invention. The illustrated cartridge has a first member 104 for sampling blood. The member 104 is movably positioned in relation to the housing 100 between two positions, a first position for blood sampling, and a second position to connect the first storage chamber 103 with the first mixing chamber 112. A blood sample is passed through the bore 122 into the first cavity of the member 104 by capillary forces or by applying a vacuum at the end of the sampling channel 111. A liquid blocking valve 116 is arranged after the first sampling member to hinder passage of blood through the channel. After the blood sampling, the sampling member is turned to the second position and the sample is flushed into the first mixing chamber 112 by the liquid in the first storage chamber 103. In the first mixing chamber 112 the sample is diluted 1:200 with the liquid in the first storage chamber 103.

The cartridge further comprises a second sampling member 124 positioned in the housing 100 for sampling a small and precise volume of liquid from the first mixing chamber 112 and having a second cavity 123 for receiving and holding the sampled liquid, the member 124 being movably positioned in relation to the housing 100 in such a way that, in a first position, the second cavity 123 is in communication with the first mixing chamber 112 for entrance of a diluted sample from the first mixing chamber 112 into the first cavity 123, and, in a second position, the second cavity 123 is in communication with the second mixing chamber 110 so that the diluted sample is flushed into the second mixing chamber 110 by the liquid in the second storage chamber 105. In the second mixing chamber 110 the sample is further diluted 1:200 to a total dilution of 1:40.000 with the liquid in the second storage chamber 105. A hemolysing reagent is injected into the first mixing chamber 112 by a piston which breaks a seal between a reagent chamber and the first mixing chamber 112. The piston, seal and reagent chamber are not shown in FIG. 9. After hemolysing the blood the 1:200 diluted sample is ready for counting non-hemolysed white blood cells and for measuring haemoglobin by photometry. The white cells are counted by passing them through a first orifice 113 and measuring the response by impedance cell counting over a first electrode pair 117, 120. A fixed volume is counted by a first volume metering arrangement 107 connected to the first collection chamber 114. A first overflow volume 106 is arranged after the first volume metering arrangement 107. The white blood cells can be differentiated by volume after adding the lysing reagent to the blood. The white cells can be grouped by volume into: Granulocytes, Monocytes and Lymphocytes. The three groups together yield the total white cell count.

In the second mixing chamber 110, red blood cells and platelets are counted. The red cells and platelets are counted by passing them through a second orifice 109 and measuring the response by impedance cell counting over a second electrode pair 121, 125. A fixed volume is counted by a second volume metering arrangement 101 connected to the second collection chamber 108. A second overflow volume 102 is placed after the second volume metering arrangement 101.

The embodiment may further comprise an additional optical detector for photometric determination of the haemoglobin content. Referred to simply as "total haemoglobin", this test involves lysing the erythrocytes, thus producing an evenly distributed solution of haemoglobin in the sample. The haemoglobin is chemically converted to the more stable and easily measured methemoglobintriazole-complex, which is a coloured compound that can be measured calorimetrically, its concentration being calculated from its amount of light absorption using Beer's Law. The method requires measurement of haemoglobin at approx. 540 nm where the absorption is high with a turbidity correction measurement at 880 nm where the absorption is low.

The invention claimed is:

1. A cartridge for counting and discriminating a plurality of types of blood cells in a blood sample in one counting operation, comprising a housing with
    a first liquid storage chamber that has prestored therein a lysing reagent that lyses erythrocytes while maintaining counting ability of other blood cell types,
    wherein the lysing reagent contains a surfactant comprising a saponin, or
    wherein the lysing reagent comprises a quaternary ammonium salt and further comprises N-(1-acetamido)iminodiacetic acid to further assist the quaternary ammonium salt in minimizing debris stemming from hemolysed red blood cells,
    a first mixing chamber and a first collection chamber separated by a wall containing a first orifice for the passage of the cells between the first mixing chamber and the first collection chamber,
    a first cell characterizer that characterizes and counts the plurality of types of blood cells passing through the first orifice, the first cell characterizer including respective electrodes in the first mixing chamber and the first collection chamber, a bore in the outer surface of the housing for entrance of the blood sample, and a first sampling member positioned in the housing for sampling the blood sample and having a first cavity for receiving and holding the blood sample, the first sampling member being movably positioned in relation to the housing in such a way that in a first position, the first cavity is in communication with the bore to receive and hold the blood sample, and in a second position, the first liquid storage chamber communicates through the first cavity with the first mixing chamber so that the blood sample held in the first cavity can be flushed with the lysing reagent prestored in the first liquid storage chamber into the first mixing chamber and mixed with the lysing reagent in the first mixing chamber.

2. A cartridge according to claim 1, wherein the first liquid storage chamber further comprises compounds selected from the group consisting of N-(1-acetamido)iminodiacetic acid, procaine hydrochloride, and 1,3-dimethylurea for stabilizing leukocytes during hemolysis of the red blood cells.

3. A cartridge according to claim 1, wherein the first liquid storage chamber further comprises compounds selected from the group consisting of N-(1-acetamido)iminodiacetic acid, sodium chloride, and sodium sulphate for adjusting pH-value and osmotic pressure of the liquid therein.

4. A cartridge according to claim 1, wherein the first liquid storage chamber further comprises compounds selected from the group consisting of 1,3-dimethylolurea and chlorhexidine diacetate for minimizing bacterial growth.

5. A cartridge according to claim 1, wherein the first liquid storage chamber further comprises compounds selected from the group consisting of potassium cyanide, tetrazole, and triazole for converting haemoglobin species to an end product suitable for spectrophotometric analysis.

6. A cartridge according to claim 1, wherein the first liquid storage chamber contains inorganic salts rendering the liquid therein as having high electrical conductivity.

7. A cartridge according to claim 1, wherein the lysing reagent comprises 1,2,4-Triazole, dodecyltrimethylammonium chloride, and hexadecyltrimethylammonium bromide.

8. A cartridge according to claim 1, wherein the other blood cell types are reduced in size, and concentration thereof is determined by counting a representative fraction of respective cells.

9. A cartridge according to claim 1, wherein the other blood cell types include lymphocytes, which are selectively reduced in size by the lysing reagent and can be counted in a cell counter.

10. A cartridge according to claim 1, further comprising:
a second mixing chamber and a second collection chamber separated by a second wall containing a second orifice for the passage of the cells between the second mixing chamber and the second collection chamber,
a second cell characterizer that characterizes and counts the plurality of types of blood cells passing through the second orifice,
wherein in the second position, the first cavity is in communication with the first mixing chamber so that liquid from the first mixing chamber can enter into the first cavity, and wherein in a third position, the first cavity is in communication with the second mixing chamber the liquid in the first cavity can be discharged into the second mixing chamber.

11. A cartridge according to claim 1, further comprising:
a second mixing chamber and a second collection chamber separated by a second wall containing a second orifice for the passage of the cells between the second mixing chamber and the second collection chamber,
a second cell characterizer that characterizes and counts the plurality of types of blood cells passing through the second orifice, and
a second sampling member positioned in the housing for sampling a small and precise volume of liquid from the first mixing chamber and having a second cavity for receiving and holding the sampled liquid, the second sampling member being movably positioned in relation to the housing in such a way that
in a first position, the second cavity is in communication with the first mixing chamber for entrance of liquid from the first mixing chamber into the second cavity, and
in a second position, the second cavity is in communication with the second mixing chamber for discharge of the sampled liquid in the second cavity into the second mixing chamber.

12. A cartridge according to claim 1, further comprising a reagent chamber positioned adjacent to the first mixing chamber for holding a reagent to be entered into the first mixing chamber.

13. A cartridge according to claim 12, further comprising a breakable seal separating the reagent chamber from the first mixing chamber.

14. A cartridge according to claim 1, wherein a mixing member is positioned in the first mixing chamber.

15. A cartridge according to claim 1, further comprising a sensor for characterization of the liquid.

16. A cartridge according to claim 15, wherein the sensor for characterization of the liquid is adapted for spectrophotometric characterization of the liquid.

17. A cartridge according to claim 1, wherein the first orifice has a diameter in the range from 30 µm to 100 µm.

18. A cartridge according to claim 17, wherein the diameter of the first orifice is in the range from 35 µm to 50 µm.

19. A cartridge according to claim 17, wherein the diameter of the first orifice is in the range from 30 µm to 45 µm.

20. A cartridge according to claim 19, wherein the diameter of the first orifice is in the range from 35 µm to 40 µm.

21. A cartridge according to claim 20, wherein the diameter of the first orifice is substantially equal to 40 µm.

22. A cartridge according to claim 1, wherein the other blood cell types include monocytes, which are selectively reduced in size by the lysing reagent and can be counted in a cell counter.

23. A cartridge according to claim 1, wherein the other blood cell types include granulocytes, which are selectively reduced in size by the lysing reagent and can be counted in a cell counter.

24. A cartridge for counting and discriminating a plurality of types of blood cells in a blood sample in one counting operation, comprising a housing with
a first liquid storage chamber that holds a lysing reagent that lyses erythrocytes while maintaining counting ability of other blood cell types,
wherein the lysing reagent contains a surfactant comprising a saponin, or wherein the lysing reagent comprises a quaternary ammonium salt and further comprises N-(1-acetamido)iminodiacetic acid to further assist the quaternary ammonium salt in minimizing debris stemming from hemolysed red blood cells, a first mixing chamber and a first collection chamber separated by a wall containing a first orifice for the passage of the cells between the first mixing chamber and the first collection chamber, a first cell characterizer that characterizes and counts the plurality of types of blood cells passing through the first orifice, the first cell characterizer including respective electrodes in the first mixing chamber and the first collection chamber, a bore in the outer surface of the housing for entrance of the blood sample, and a first sampling member positioned in the housing for sampling the blood sample and having a first cavity for receiving and holding the blood sample, the first sampling member being movably positioned in relation to the housing in such a way that,
  in a first position, the first cavity is in communication with the bore to receive and hold the blood sample, and
  in a second position, the first liquid storage chamber communicates through the first cavity with the first mixing chamber so that the blood sample can be flushed with the lysing reagent from the first liquid storage chamber into the first mixing chamber, wherein the cartridge comprises a pressure channel communicating with the first collection chamber, the pressure channel being adapted for coupling to a pressure source such that liquid flow through the first orifice can be controlled by pressure applied by the pressure source.

25. A cartridge for counting and discriminating a plurality of types of blood cells in a blood sample in one counting operation, comprising a housing with
  a first liquid storage chamber that holds a lysing reagent that lyses erythrocytes while maintaining counting ability of other blood cell types,
  wherein the lysing reagent contains a surfactant comprising a saponin, or
  wherein the lysing reagent comprises a quaternary ammonium salt and further comprises N-(1-acetamido)iminodiacetic acid to further assist the quaternary ammonium salt in minimizing debris stemming from hemolysed red blood cells, a first mixing chamber and a first collection chamber separated by a wall containing a first orifice for the passage of the cells between the first mixing chamber and the first collection chamber, a first cell characterizer that characterizes and counts the plurality of types of blood cells passing through the first orifice, the first cell characterizer including respective electrodes in the first mixing chamber and the first collection chamber, a bore in the outer surface of the housing for entrance of the blood sample, and a first sampling member positioned in the housing for sampling the blood sample and having a first cavity for receiving and holding the blood sample, the first sampling member being movably positioned in relation to the housing in such a way that
  in a first position, the first cavity is in communication with the bore to receive and hold the blood sample, and
  in a second position, the first liquid storage chamber communicates through the first cavity with the first mixing chamber so that the blood sample can be flushed with the lysing reagent from the first liquid storage chamber into the first mixing chamber, wherein the cartridge comprises a pressure channel leading from the first mixing chamber and communicating with a first fluid connection port in the cartridge, the first fluid connection port being adapted for coupling to fluid pressure through a second fluid connection port of a docking station, such that liquid flow through the cartridge is controllable by the fluid pressure applied by a pressure source within the docking station.

* * * * *